United States Patent [19]

Taraschi et al.

[11] Patent Number: 5,356,927

[45] Date of Patent: Oct. 18, 1994

[54] METHODS OF TREATING PLASMODIUM AND BABESIA PARASITIC INFECTIONS

[75] Inventors: Theodore F. Taraschi, Tabernacle, N.J.; Bruno Pouvelle, Philadelphia, Pa.

[73] Assignee: Thomas Jefferson University, Philadelphia, Pa.

[21] Appl. No.: 984,915

[22] Filed: Dec. 2, 1992

[51] Int. Cl.$^5$ .......................................... A61K 31/335
[52] U.S. Cl. ..................................... 514/449; 514/895
[58] Field of Search ................................ 514/449, 895

[56] References Cited

U.S. PATENT DOCUMENTS

| | | | |
|---|---|---|---|
| 4,814,470 | 3/1989 | Colin et al. | 514/449 |
| 4,857,653 | 8/1989 | Colin et al. | 549/511 |
| 4,876,399 | 10/1989 | Holton et al. | 568/817 |
| 4,924,011 | 5/1990 | Denis et al. | 549/510 |
| 4,942,184 | 7/1990 | Haugwitz et al. | 514/449 |
| 4,960,790 | 10/1990 | Stella et al. | 514/449 |
| 5,015,744 | 5/1991 | Holton | 549/510 |
| 5,019,504 | 5/1991 | Christen et al. | 435/123 |
| 5,059,699 | 10/1991 | Kingston et al. | 549/511 |

OTHER PUBLICATIONS

Singleton et al., "*Dictionary of Microbiology and Molecular Biology*" (2nd Ed.), published by John Wiley & Sons pp. 239, 468, 494, 688, 790 and 898 (1987).

Denis et al., "Direct, Highly Efficient Synthesis from (S)-(+)-Phenylglycine of the Taxol and Taxotere Side Chains", *J. Org. Chem.* 56: 6939-6942 (1991).

Baum, et al. *Proceedings of the National Academy of Science, U.S.A.,* 1981, 78, 4571-4575.

Kumar et al., "Plasmodium gallinaceum: Critical Role For Microtubules . . . " Experimental Parasitology, 59(2), pp. 239-247 (Apr. 1985).

Dieckmann-Schuppert et al., "Mode of Action of Tubulozoles Against Plasmodium Falciparum In Vitro", Antimicrobial Agents and Chemotherapy, Aug. 1990, vol. 34, No. 8, pp. 1529-1534.

Embase Abstract No: 85110113, 1985, Kumar et al., "Plasmodium gallinaceum: Critical role . . . ".

Fuerst, *Frobisher and Fuerst's Microbiology in Health and Disease,* Chapter 41, W.B. Saunders Company, 1983, USA, pp. 600-605.

*Primary Examiner*—Marianne M. Cintins
*Assistant Examiner*—M. Moezie
*Attorney, Agent, or Firm*—Woodcock Washburn Kurtz Mackiewicz & Norris

[57] ABSTRACT

Methods of inhibiting the proliferation of Plasmodium or Babesia parasites are provided by the present invention. Such methods may be useful for treating malaria and babesiosis in mammals such as humans.

2 Claims, 6 Drawing Sheets

METHODS OF TREATING PLASMODIUM AND BABESIA PARASITIC INFECTIONS

BACKGROUND OF THE INVENTION

Human malaria, caused by a protozoan sporozoa, is an acute and chronic protozoal disease caused by four species of plasmodia, namely *Plasmodium falciparum, P. vivax, P. ovals* and *P. malarias. P. falciparum* is the most virulent of these and the only one that kills acutely. The plasmodial parasites are transmitted by female mosquitoes of several species of the genus Anopheles. The World Health Organization recognizes malaria as the world's major primary health problem, causing more morbidity and mortality than any other disease. An estimated 300–500 million cases occur annually resulting in 3–5 million deaths, mostly among children. Malaria is a serious problem mainly in the tropical and subtropical world, especially Africa, South and Central America, India and Southeast Asia. Isolated cases of malaria have recently been reported in the southeastern and southwestern United States. The drug chloroquine is often used to treat malaria, however, the rapid spread of chloroquine-resistant P. *falciparum* and the lack of a malaria vaccine emphasizes the long-felt need to develop new strategies and agents for controlling this disease.

Babesiosis, an infection by protozoan sporozoa of the genus Babesia, is transmitted by hard-bodied ticks. The causative organisms, parasites resembling those of malaria, invade and destroy erythrocytes. Babesia infections in wild and domestic animals occur worldwide and are well known in veterinary medicine. Human infections are more rare and occur exclusively in Europe and North America. In many countries, Babesia is responsible for serious economic losses to the livestock industry. No effective chemotherapeutic treatment or vaccine has been known for treatment of babesiosis.

Taxol is a diterpenoid isolated from the stem bark of the western yew, *Taxus brevifolia*. Taxol is a mitotic spindle poison that stabilizes microtubules and inhibits their depolymerization to free tubulin. Taxol has been demonstrated to possess antineoplastic activity and has been identified as an anti-cancer agent, particularly in the treatment of advanced ovarian cancer.

Over ten years ago, Baum, et al. *Proceeding of the National Academy of Science*, U.S.A., 1981, 78, 4571–4575, found that taxol inhibited the flagellate protozoan *Trypanosoa cruzi*. Trypanosomes, being flagellated protozoans, belong to the protozoal Phylum mastigophora. Baum, et al. found that the addition of taxol inhibited the replication of *T. cruzi* in a dose-dependent fashion. Baum. et al. treated cultures containing trypanosomes with 1 nM to 10 µM of taxol. However, treatment of trypanosomiasis was never developed and there are presently no efficacious and safe drugs for treating these infections, particularly the chronic forms.

Treatments for malaria and babesiosis have been similarly disappointing. Methods which are known for the treatment of malaria and babesiosis have not been satisfactory due to expense, limited efficacy, drug resistance, and safety. Methods for the treatment of malaria and babesiosis infections are greatly needed. The present invention provides methods satisfying this long-felt need.

SUMMARY OF THE INVENTION

Treatment of malaria and babesiosis has been problematic due to the lack of effective agents which are at once inexpensive, efficacious, and safe. The currently available drugs used to treat malaria all act by similar mechanisms, i e , acidification of the parasite's food vacuole or inhibition of parasite enzymes. Due to the chemical similarity of the agents (e.g. aminoquinolines or pyrlmethamine) strains of Plasmodium have rapidly developed drug resistance and have created a need for new and novel methods of treating Plasmodium infections.

The present invention provides methods of inhibiting the proliferation of a Plasmodium parasite comprising contacting the Plasmodium parasite with an amount of taxol effective to inhibit the proliferation of said parasite.

The present invention provides methods of inhibiting the proliferation of a Babesia parasite comprising contacting the Babesia parasite with an amount of taxol effective to kill the parasite.

The present invention further provides methods of inhibiting the proliferation of Plasmodium and Babesia parasites in a cell comprising contacting the cell with from about 0.1 µM to about 1 µM taxol.

The present invention also provides methods of treating Plasmodium and Babesia infections in a mammal comprising administering to a mammal a therapeutically effective amount of taxol.

These methods represents an entirely new rationale for treating malaria and babesiosis infections by inhibiting spindle formation during mitosis and preventing the formation of nascent infectious merozoites during the erythrocyte phase.

DETAILED DESCRIPTION OF THE INVENTION

Figure 1:
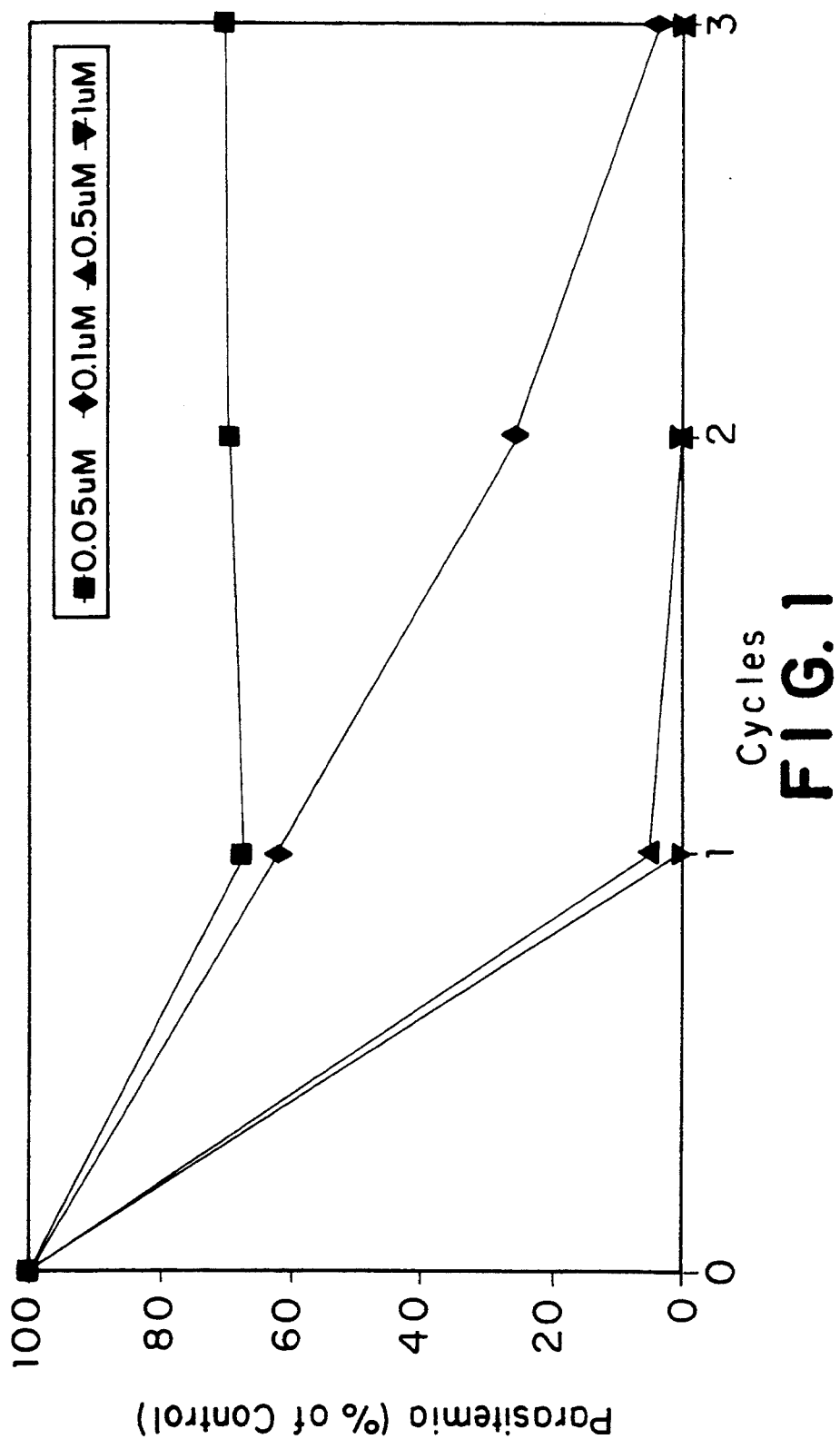
FIG. 1 is a schematic representation of the effect of taxol on human erythrocytes infected with drug sensitive FCR3-C5 malaria clones.

The present invention provides methods of inhibiting the proliferation of Plasmodium and Babesia comprising contacting the parasite with an amount of taxol effective to inhibit the proliferation of the parasite. In other embodiments of the present invention the proliferation of Plasmodium and Babesia parasites in a cell may be inhibited by contacting the cell with from about 0.1 µM to about 1 µM taxol. In still other embodiments of the present invention malaria and babesiosis infection in a mammal can be treated by administering to a mammal suffering from such an infection a therapeutically effective amount of taxol or a derivative thereof.

Taxol is a compound which has been known for use as an anti-cancer agent. Generally, taxol is known to promote tubulin assembly into stable aggregated structures which resist depolymerization. While not wishing to be bound to any particular theory, it is believed that taxol blocks the production of nascent infectious merozoites by binding to parasite microtubules and preventing proper spindle formation and nuclear division during schizogny. Thus, it is believed that non-nucleated merozoites result which are no longer capable of infecting erythrocytes.

Taxol is commercially available or may be prepared such as by methods described by Holton, U.S. Pat. No. 4,876,399, issued Oct. 24, 1989; Colin, et al., U.S. Pat. No. 4,814,470, issued Mar. 21, 1989; Colin, et al., U.S. Pat. No. 4,857,653, issued Aug. 15, 1989; Holton, U.S. Pat. No. 5,015,744, issued May 14, 1991; and Denis, et al., U.S. Pat. No. 4,924,011, issued May 8, 1990, the disclosures of which are incorporated by reference herein in their entirety. By the term taxol is also meant precursors, derivatives and analogues of taxol, for example taxotere. All precursors, derivatives and analogues of taxol which are functionally interchangeable with taxol, yet structurally distinct are encompassed by the present invention. For example, water soluble derivatives of taxol are encompassed by the present invention. Some derivatives of taxol are described by Holton, et al., U.S. Pat. No. 4,876,399 issued Oct. 24, 1989; Haugwitz, et al., U.S. Pat. No. 4,942,184 issued Jul. 17, 1990; Christen, et al., U.S. Pat. No. 5,019,504, issued May 28, 1991; Kingston, et al., U.S. Pat. No. 5,059,699, issued Oct. 22, 1991; and Stella, et al., U.S. Pat. No. 4,960,790 issued Oct. 2, 1990, the disclosures of which are incorporated by reference herein in their entirety. Of course, any composition which binds toparasite microtubules thereby preventing proper spindle formation and nuclear division during schizogny could be effectively used in some methods of the present invention.

In some embodiments of the present invention from about 0.1 $\mu$M to about 1 $\mu$M taxol effectively inhibits the proliferation Plasmodium or Babesia parasites. Preferably 1 $\mu$M taxol is contacted with a Plasmodium or Babesia parasite.

Cells infected with Plasmodium or Babesia may also be treated with from about 0.1 $\mu$M to about 1 $\mu$M taxol to eliminate or reduce the infection. In preferred embodiments of the present invention 10 to 100 times lower plasma concentrations of taxol will be therapeutically effective for the treatment of malaria and babesiosis than is necessary for anti-neoplastic treatment. Therapeutically effective amounts are those amounts which reduce, or eliminate a malaria or babesiosis infection. Any reduction in the infection is therapeutic. Thus 10% of the parasites may be killed in accordance with some embodiments of the present invention. In preferred embodiments of the present invention a therapeutic or effective amount of taxol effectively kills from about 50% to 100% of the parasites. In still more preferred embodiments at least 80% of the parasites are killed. In yet more preferred embodiments of the present invention at least 90% of the parasites are killed. In most preferred embodiments of the present invention 100% of the parasites are killed.

In some preferred embodiments of the present invention from about 0.01 $\mu$M to about 1.0 $\mu$M plasma concentration of taxol is envisioned for therapeutic treatment of Plasmodium or Babesia infection in a mammal.

In more preferred embodiments of the present invention from about 0.05 $\mu$M plasma concentration of taxol to about 0.1 $\mu$M plasma concentration of taxol is envisioned for therapeutic treatment of Plasmodium or Babesia infection in a mammal.

One skilled in the art would also be familiar with methods of administration which may be effective for treatment of parasite infections in view of the present disclosure. For example administration may be carried out intravascularly, orally, rectally, etc., using a variety of dosage forms. In preferred embodiments of the present invention taxol is administered by infusion. In some instances, it may be desireable to administer taxol in conjunction with other drugs or formulations. Thus, taxol may be administered bound to human serum albumin or encapsulated in liposomes in some embodiments of the present invention.

Treatment is performed until the desired therapeutic result, i.e. reduction or elimination of parasite infection, is achieved. Preferably, treatment is performed for from about 8 to about 48 hours. Treatment for the duration of from about 48 to about 144 hours may be effective in some embodiments of the present invention. In other embodiments of the present invention shorter durations may be useful, for instance, a single bolus may be sufficient in some cases to reduce or eliminate parasite infection.

One skilled in the art will recognize that the useful dosage, within the range identified, may be administered and the particular mode of administration, dosage, and duration will vary depending upon the age, weight and condition of the patient.

The following examples are illustrative, but are not meant to be limiting of the present invention.

EXAMPLES

EXAMPLE 1 - CULTURES

Different strains of cloned malaria parasites (FCR3-C5, ITG2-G1, Palo Alto, 3D7, HB3, 7G8 T9-94) were grown in tissue culture by the candle jar method at 5% hematocrit (FCR3-C5) or in Falcon tissue culture flasks gassed with 94% $N_2$, 5% $CO_2$, 1% $O_2$ at 3%! hematocrit (ITG2-G1, Palo Alto, 3D7, HB3, 7G8, T9-94). The! tissue culture medium consisted of RPMI 1640 supplemented with 24 mM $NaHCO_3$, 25 mM Hepes, 21.1 mM dextrose, 2 mM glutathione, 0.44 mM hypoxanthine and 66 mg/l gentamycin and 10% heat-inactivated human serum. T9-94 is chloroquine resistant, 7G8 is chloroquine and pyrimethamine resistant and HB3 is pyrimethamine resistant. The drug resistant parasites were obtained from Dr. David Walliker at the University of Edinburgh, United Kingdom. Taxol, obtained from Molecular Probes, Inc., Eugene, Oregon (Catalogue #T-3456) is dissolved in dimethyl sulfoxide (DMSO).

EXAMPLE 2 - TAXOL

Taxol is supplied as a concentrated sterile solution 6 mg/ml (7.02 nM) in a 5 ml ampule (30 mg/ampule), in polyoxyethylated castor oil (Cremophor EL), 50% and dehydrated alcohol USP, 50%. Prior to administration, the drug is further diluted in 1 l of 5% dextrose in water. On the basis of clinical observations, the National Cancer Institute recommends 24 h infusions along with prophylactic antiallergic premedications (i.e. dexamethasone, diphenhydramine and cimetidine or ranitidine).

Pharmacology studies have been performed on patients with a variety of cancers who were infused continuously intravenously (i.v.) for 6 h at a dose of 230 mg/m$^2$. Drug plasma concentrations increase throughout the 6 h infusion and decline immediately upon cessation of the infusion. Plasma disappearance curves are biphasic, with an $\alpha$ and $\beta t_{\frac{1}{2}}$ of 0.42 and 8.4 h, respectively. Peak plasma concentrations ranged from 2–10 $\mu$M. Taxol binds extensively to plasma proteins (90–95%) and is systemically cleared by metabolism, biliary excretion and/or extensive tissue binding. The major side effects at these dosages include neutropenia and hypersensitivity, which are manageable.

EXAMPLE 3

Cultures of human erythrocytes infected with the FCR3-C5 (Gambian, chloroquine and pyrimethamine sensitive) clone of *Plasmodium falciparum* were grown in the absence and presence of taxol at concentrations ranging from 0.05 $\mu$M to 1 $\mu$M. Taxol was added 4 hours post-invasion and maintained in cultures for three life cycles. Each life cycle is approximately 48 hours in duration. A life cycle is the time during which intracellar parasites undergo asexual development and merozoites are released to produce new infections. Parasitemia is defined as the number of infected erythrocytes divided by the total number of erythrocytes $\times$ 100. The efficacy of taxol, expressed as Parasitemia (% of control) was determined by counting the parasitemia in treated cultures 10 hours after invasion was completed in the control, untreated cultures and comparing it to the parasitemia of the untreated control cultures. A parasitemia of 0% indicate that taxol totally inhibits new infections; a parasitemia of 100% indicates that taxol has no effect.

As shown in FIG. 1, during the first cycle, 0.05 $\mu$M and 0.1 $\mu$M reduces the parasitemia by 30–40%, 0.5 $\mu$M by 95% and 1.0 $\mu$M by 100%. During the second life cycle 0.05 $\mu$M reduced parasitemia by 35%, 0.1 $\mu$M by 75% and 0.5 and 1 $\mu$M by 100%. After three cycles, 0.05 $\mu$M reduced parasitemia by 30% and 0.1, 0.5 and 1.0 $\mu$M by 100%.

EXAMPLE 4

Figure 2:
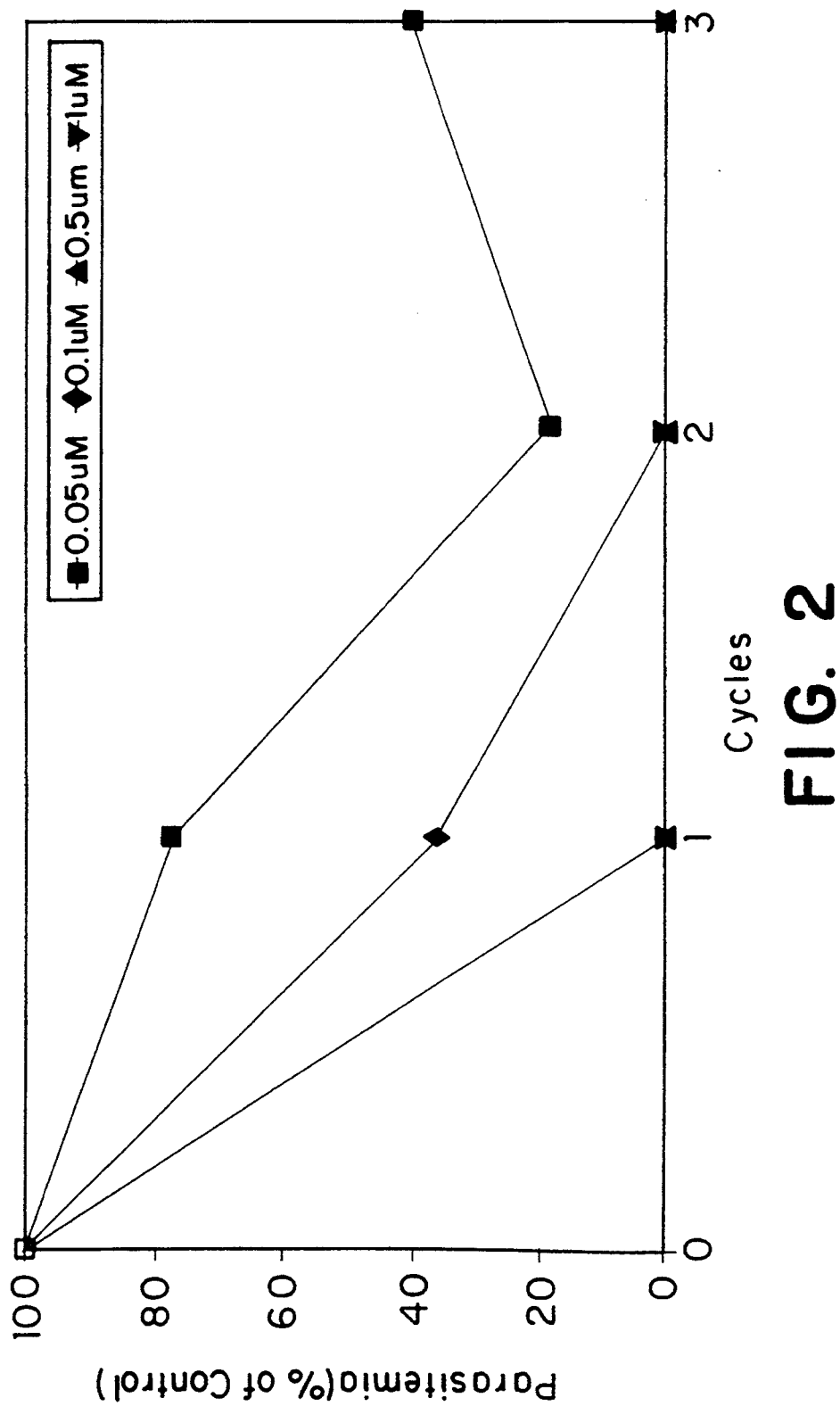
FIG. 2 is a schematic representation of the effect of taxol on chloroquine sensitive, pyrimethamine resistant HB3 malaria clones.

Cultures of human erythrocytes infected with HB3 (Honduras, chloroquine sensitive, pyrimethamine resistant) clone of *Plasmodium falciparum* were grown in the absence and presence of taxol at concentrations ranging from 0.05 to 1 $\mu$M. Taxol was added 4 hours post-invasion and maintained in cultures for three life cycles. Each life cycle is approximately 48 hours in duration. Parasitemia is defined as the number of infected erythrocytes divided by the total number of erythrocytes $\times$ 100. The efficacy of taxol, expressed as Parasitemia (% of control) was determined by counting the parasitemia in treated cultures 10 hours after invasion was completed in the control, untreated cultures and comparing it to the parasitemia of the untreated control cultures. A parasitemia of 0% indicate that taxol totally inhibits new infections; a parasitemia of 100% indicates that taxol has no effect. As shown in FIG. 2, during the first cycle, 0.05 $\mu$M taxol reduces the parasitemia by 20%, 0.1 by 60%, and 0.5 mM and 1.0 $\mu$M by 100%. During the second cycle, 0.05 $\mu$M reduces parasitemia by 80%, and 0.1, 0.5 and 1 $\mu$m by 100%.

EXAMPLE 5

Figure 3:
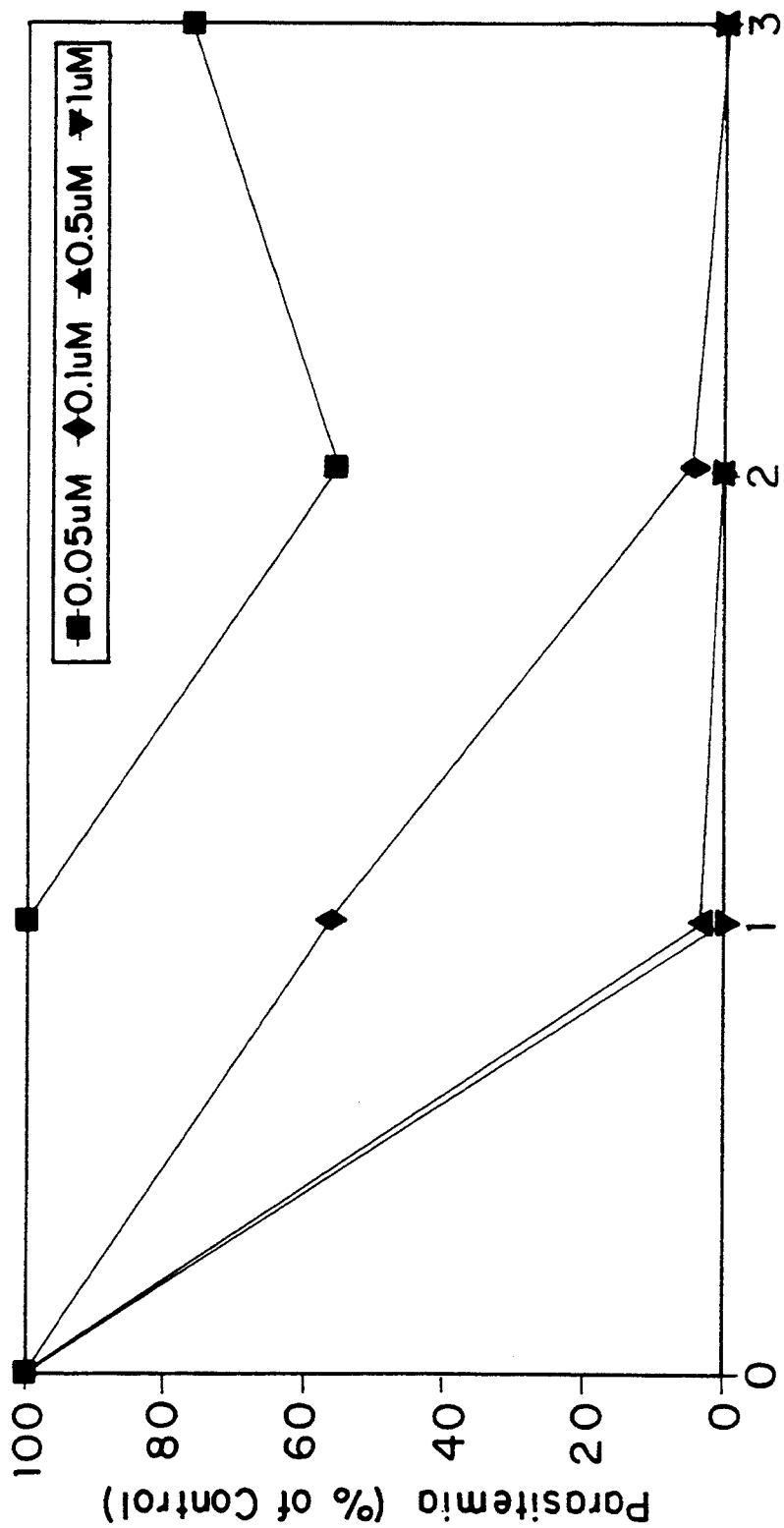
FIG. 3 is a schematic representation of the effect of taxol on chloroquine resistant, pyrimethamine sensitive T9-94 malaria clones.

Cultures of human erythrocytes infected with T9-94 (Thailand, chloroquine resistant and pyrimethamine sensitive) clone of *Plasmodium falciparum* were grown in the absence and presence of taxol at concentrations ranging from 0.05 to 1 $\mu$M. Taxol was added 4 hours post-invasion and maintained in cultures for three life cycles. Each life cycle is approximately 48 hours in duration. Parasitemia is defined as the number of infected erythrocytes divided by the total number of erythrocytes $\times$ 100. The efficacy of taxol, expressed as Parasitemia (% of control) was determined by counting the parasitemia in treated cultures 10 hours after invasion was completed in the control, untreated cultures and comparing it to the parasitemia of the untreated control cultures. A parasitemia of 0% indicate that taxol totally inhibits new infections; a parasitemia of 100% indicates that taxol has no effect. As shown in FIG. 3, during the first cycle, 0.05 $\mu$M had no effect, 0.1 $\mu$M taxol reduced the parasitemia by 30–40%, 0.5 $\mu$M by 95%, and 1.0 $\mu$M by 100%. During the second cycle, 0.05 $\mu$M reduced parasitemia by 40%, 0.1 $\mu$M by 95%, and 0.5 and 1 $\mu$M by 100%. After 3 cycles, 0.05 $\mu$M reduced parasitemia by 20% and 0.1, 0.5, and 1.0 $\mu$M by 100%.

EXAMPLE 6

Figure 4:
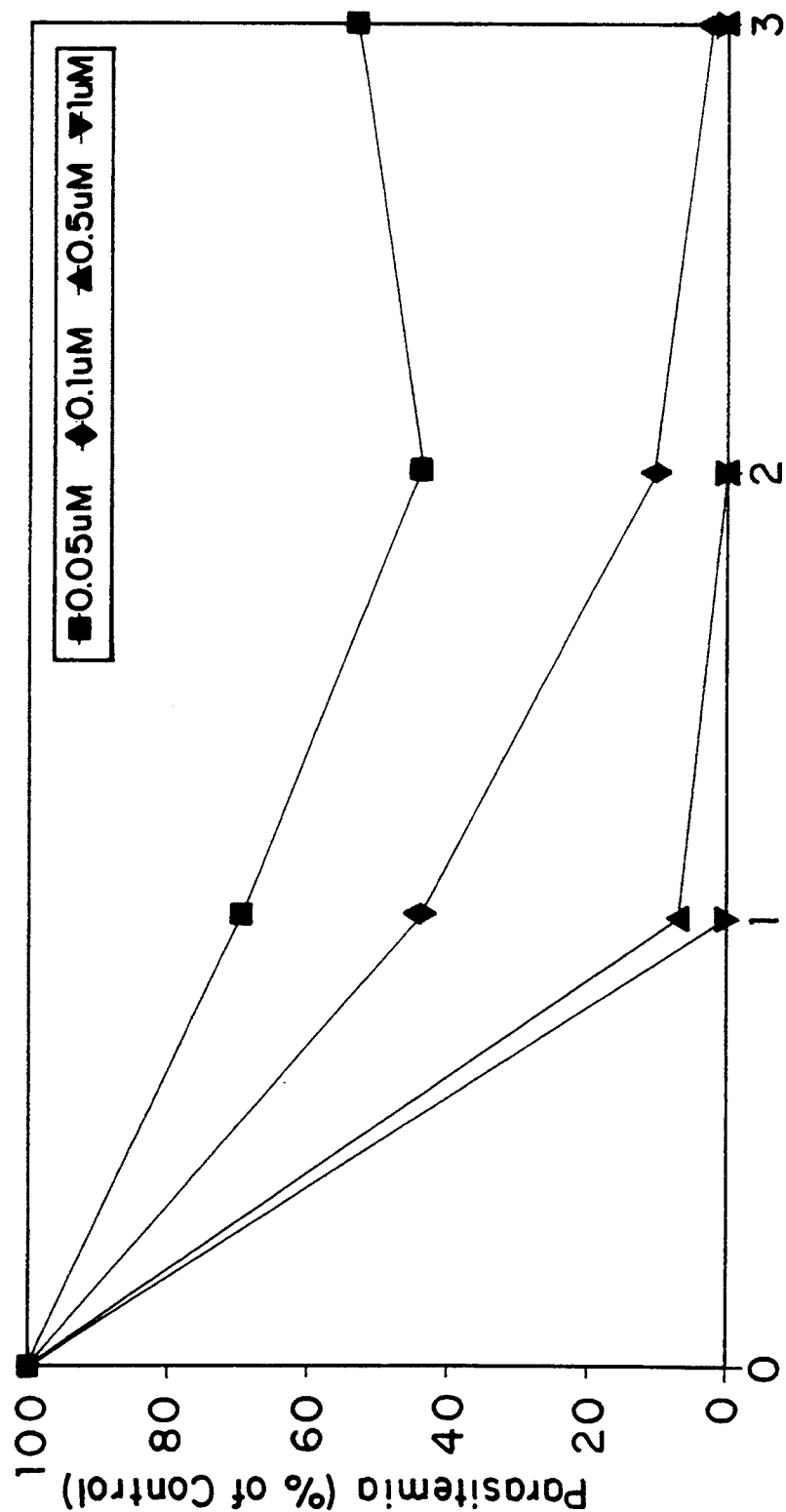
FIG. 4 is a schematic representation of chloroquine resistant, pyrimethamine resistant, 7G8 malaria clones.

Cultures of human erythrocytes infected with 7G8 (Brazil, chloroquine and pyrimethane resistant) clone of *Plasmodium falciparum* were grown in the absence and presence of taxol at concentrations ranging from 0.05 to 1 $\mu$M. Taxol was added 4 hours post-invasion and maintained in cultures for three life cycles. Each life cycle is approximately 48 hours in duration. Parasitemia is defined as the number of infected erythrocytes divided by the total number of erythrocytes $\times$ 100. The efficacy of taxol, expressed as Parasitemia (% of control) was determined by counting the parasitemia in treated cultures 10 hours after invasion was completed in the control, untreated cultures and comparing it to the parasitemia of the untreated control cultures. A parasitemia of 0% indicate that taxol totally inhibits new infections; a parasitemia of 100% indicates that taxol has no effect. As shown in FIG. 4, during the first cycle, 0.05 $\mu$M taxol reduced parasitemia by 30%, 0.1 reduced parasitemia by 50-60%, 0.5 $\mu$M hy 95% and 1.0 $\mu$M by 100%, During the second cycle, 0.05 $\mu$M reduced parasitemia by 50-60%, 0.1 $\mu$M by 90%, and 0.5 and 1 $\mu$M by 100%. After 3 cycles, 0.05 $\mu$M reduced parasitemia by 40%, and 0.1, 0.5, and 1.0 $\mu$M by 100%.

EXAMPLE 7

Figure 5:
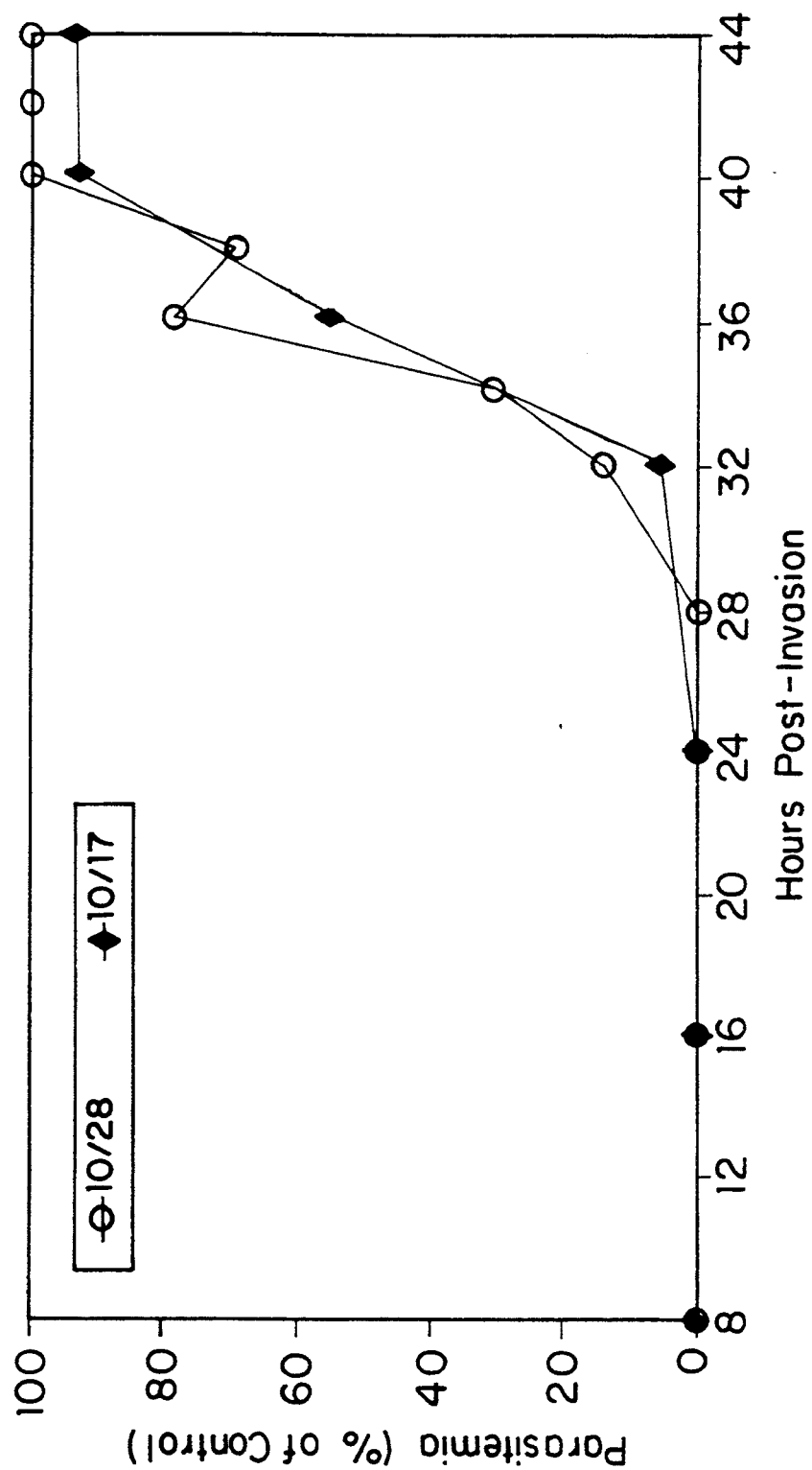
FIG. 5 is a schematic representation of the time course of taxol treatment necessary for the inhibition of new infections after 1 life cycle.

1.0 $\mu$M taxol was added to cultures of human erythrocytes infected with FCR3-C5 strain of *P. falciparum* at 8, 16, 24, 28, 32, 34, 36, 38, 40, 42, and 44 hours post-invasion. The parasitemia was counted 10 hours after the end of the first cycle and compared to an untreated control culture. As shown in FIG. 5, taxol added up to 30 hours post-invasion completely blocks the formation of new infections. Effectiveness decreases between 30 and 40 hours as would be expected since asexual mitosis and the formation of new merozoites occurs during this time in the life cycle.

EXAMPLE 8

Figure 6:
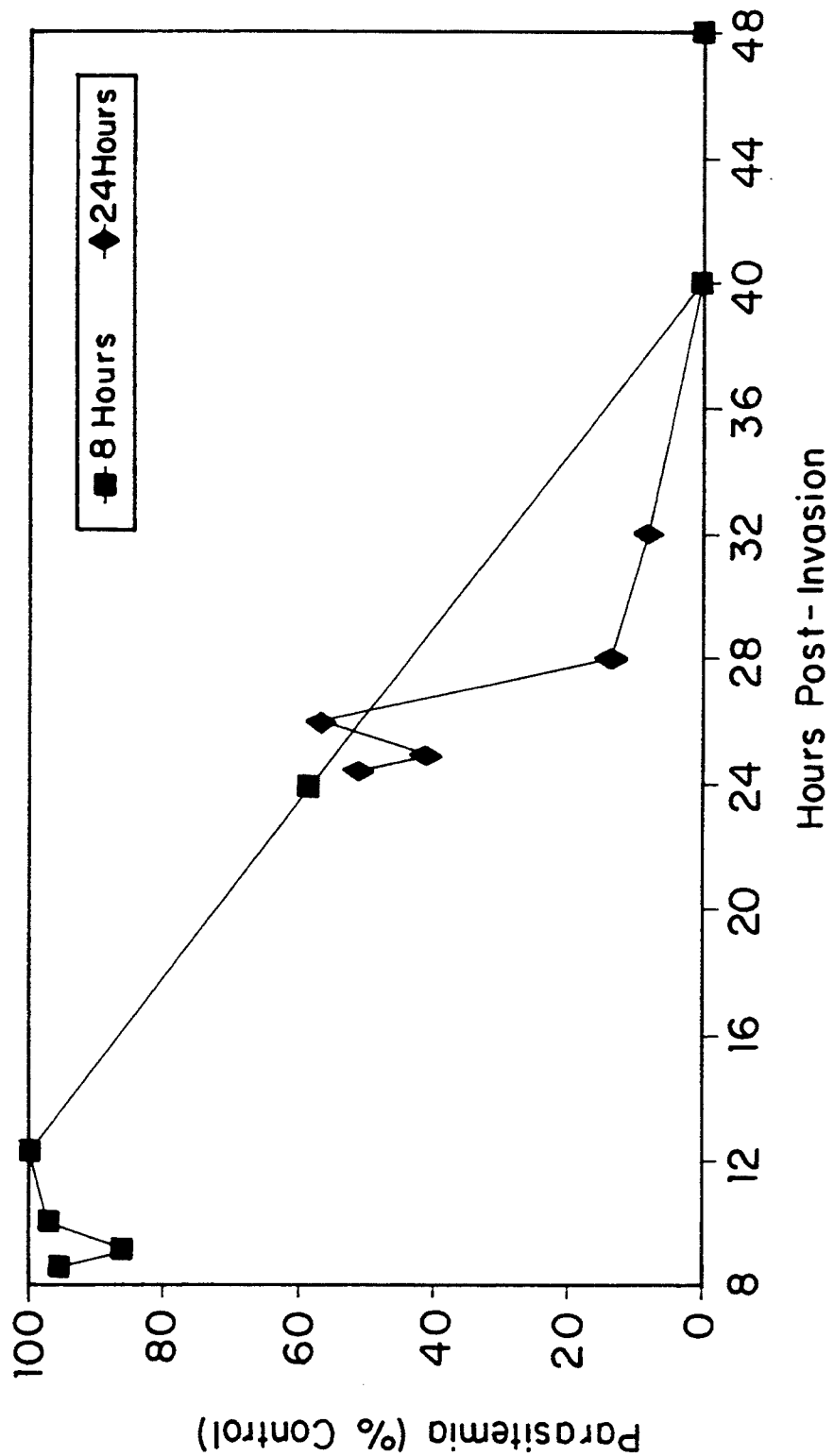
FIG. 6 is a schematic representation of the duration of taxol treatment necessary for the inhibition of new infections.

Cultures of human erythrocytes infected with the FCR3-C5 strain of *P., falciparum* were treated with 1.0

μM taxol at 8 or 24 hours post invasion. Taxol was removed from the cultures at the time points indicated and the parasitemia was measured 10 hours after re-invasion was complete in an untreated control culture. As shown in FIG. 6, taxol added at 24 hours need only be in culture for 8 hours to totally block the formation of new infections.

What is claimed is:

1. A method of treating a Plasmodium or Babesia infection in a mammal comprising administering to a mammal suffering from a Plasmodium or Babesia infection a therapeutically effective amount of taxol.

2. The method of claim 1 wherein the mammal is a human.

* * * * *

UNITED STATES PATENT AND TRADEMARK OFFICE
CERTIFICATE OF CORRECTION

PATENT NO. : 5,356,927
DATED : October 18, 1994
INVENTOR(S) : Taraschi et al.

It is certified that error appears in the above-indentified patent and that said Letters Patent is hereby corrected as shown below:

At Column 1, before Section entitled "BACKGROUND OF THE INVENTION", please insert a new section entitled -- GOVERNMENT RIGHTS -- Then on the following line please insert -- This work was funded in part by NIH Grant #AI27247. The U.S. Government may have certain rights in the invention. --

At Column 2, SUMMARY OF THE INVENTION, line 32, please delete "represents" and insert -- represent -- therefor.

At Column 3, line 38, please delete "toparasite" and insert -- to parasite -- therefor.

At Column 4, line 64, please delete "11" and insert -- 1 1 -- therefor.

Signed and Sealed this

Twenty-first Day of February, 1995

Attest:

BRUCE LEHMAN

Attesting Officer     Commissioner of Patents and Trademarks